United States Patent [19]
Goicoechea

[11] Patent Number: 6,010,530
[45] Date of Patent: Jan. 4, 2000

[54] SELF-EXPANDING ENDOLUMINAL PROSTHESIS

[75] Inventor: George Goicoechea, Freeport, Bahamas

[73] Assignee: Boston Scientific Technology, Inc., Freeport

[21] Appl. No.: 09/025,489

[22] Filed: Feb. 18, 1998

Related U.S. Application Data

[63] Continuation of application No. 08/485,015, Jun. 7, 1995, abandoned.

[51] Int. Cl.$^7$ ..................................................... A61F 2/06
[52] U.S. Cl. ................................................................. 623/1
[58] Field of Search .................................... 623/1, 11, 12; 606/194, 198

[56] References Cited

U.S. PATENT DOCUMENTS

| | | |
|---|---|---|
| 3,500,820 | 3/1970 | Almen . |
| 3,868,956 | 3/1975 | Alfidi et al. . |
| 3,878,565 | 4/1975 | Sauvage . |
| 3,890,977 | 6/1975 | Wilson . |
| 3,918,736 | 11/1975 | Vallbracht . |
| 3,996,938 | 12/1976 | Clark, III . |
| 4,149,911 | 4/1979 | Clabburn . |
| 4,306,318 | 12/1981 | Mano et al. . |
| 4,425,908 | 1/1984 | Simon . |
| 4,441,215 | 4/1984 | Kaster .......................................... 3/1.4 |
| 4,503,569 | 3/1985 | Dotter . |
| 4,512,338 | 4/1985 | Balko et al. . |
| 4,553,545 | 11/1985 | Maass et al. . |
| 4,560,374 | 12/1985 | Hammerslag . |
| 4,577,631 | 3/1986 | Kraemer . |
| 4,580,568 | 4/1986 | Gianturco . |
| 4,604,762 | 8/1986 | Robinson . |
| 4,649,922 | 3/1987 | Wiktor . |
| 4,655,771 | 4/1987 | Wallsten . |
| 4,665,906 | 5/1987 | Jervis . |
| 4,665,918 | 5/1987 | Garza et al. . |

(List continued on next page.)

FOREIGN PATENT DOCUMENTS

| | | | |
|---|---|---|---|
| 423916 | 4/1991 | European Pat. Off. | ................... 623/1 |
| 0 508 473 A2 | 10/1992 | European Pat. Off. . | |
| 0-621-015 A1 | 10/1994 | European Pat. Off. . | |
| 0 466 518 B1 | 1/1996 | European Pat. Off. . | |
| 1 491 202 | 10/1973 | United Kingdom . | |
| 2-106-190 | 4/1983 | United Kingdom . | |
| WO91/07928 | 6/1991 | WIPO . | |
| WO92/00043 | 1/1992 | WIPO . | |
| 94024961 | 11/1994 | WIPO | ....................................... 623/1 |

OTHER PUBLICATIONS

Dotter et al., "Transluminal Expandable Nitinol Coil Stent Grafting: Preliminary Report", Technical Developments and Instrumentation, Radiology, vol. 147, pp. 259–260 (Apr. 1983).

Schetky, "Shape–Memory Alloys", pp. 74–82.

K. Otsuka et al., "Shape–Memory Alloys–Pseudoelasticity". *Metal Forum*, vol. 4, No. 3, pp. 142–152 (1981).

Cragg, et al., "Nonsurgical Placement of Arterial Endoprostheses: A New Technique Using Nitinol Wire", Radiology, vol. 147, No. 1, pp. 261–263 (Apr. 1983).

Cragg, et al. "Percutaneous Arterial Grafting", Radiology, vol. 150, No. 1, pp. 45–49 (1984).

T.W. Duerig et al., "An Engineer's Perspective of Pseudoelasticity", pp. 369–393.

Cragg, et al.,"Stens/Vascular Stents", Interventional Radiology, pp. 686–692 (1990).

L. Charnsangavej et al., "Percutaneous Endovascular Graft: An Experimental Evaluation", (Abstract), Radiology, May 1987, pp. 357–360.

*Primary Examiner*—Jeffrey A. Smith
*Assistant Examiner*—Eduardo C. Robert
*Attorney, Agent, or Firm*—Ratner & Prestia

[57] ABSTRACT

An endovascular prosthesis formed of a support member with or without a continuous skin totally encapsulating the support member. The skin can include drugs or other leaching agents, or radiopaque material. A portion of the prosthesis can be tapered to fit within a tapered artery. The prosthesis is particularly adapted for use in small caliber arteries.

18 Claims, 2 Drawing Sheets

U.S. PATENT DOCUMENTS

| | | |
|---|---|---|
| 4,681,110 | 7/1987 | Wiktor . |
| 4,729,766 | 3/1988 | Bergentz et al. . |
| 4,732,152 | 3/1988 | Wallsten et al. . |
| 4,733,665 | 3/1988 | Palmaz . |
| 4,739,762 | 4/1988 | Palmaz . |
| 4,762,128 | 8/1988 | Rosenbluth . |
| 4,768,507 | 9/1988 | Fischell et al. . |
| 4,772,264 | 9/1988 | Cragg . |
| 4,776,337 | 10/1988 | Palmaz ........................................ 623/1 |
| 4,800,882 | 1/1989 | Gianturco . |
| 4,820,298 | 4/1989 | Leveen et al. . |
| 4,830,003 | 5/1989 | Wolff et al. . |
| 4,856,516 | 8/1989 | Hillstead . |
| 4,878,906 | 11/1989 | Lindemann et al. . |
| 4,886,062 | 12/1989 | Wiktor . |
| 4,913,141 | 4/1990 | Hillstead . |
| 4,922,905 | 5/1990 | Strecker . |
| 4,969,458 | 11/1990 | Wiktor . |
| 4,994,032 | 2/1991 | Sugiyama et al. . |
| 5,019,090 | 5/1991 | Pinchuk ................................. 606/194 |
| 5,024,671 | 6/1991 | Tu et al. . |
| 5,041,126 | 8/1991 | Gianturco . |
| 5,057,092 | 10/1991 | Webster, Jr. . |
| 5,067,957 | 11/1991 | Jervis . |
| 5,078,726 | 1/1992 | Kreamer . |
| 5,078,736 | 1/1992 | Behl ............................................ 623/1 |
| 5,085,635 | 2/1992 | Cragg . |
| 5,102,417 | 4/1992 | Palmaz . |
| 5,123,917 | 6/1992 | Lee . |
| 5,133,732 | 7/1992 | Wiktor . |
| 5,135,536 | 8/1992 | Hillstead . |
| 5,147,370 | 9/1992 | McNamara et al. .................... 606/108 |
| 5,282,824 | 2/1994 | Gianturco . |
| 5,364,354 | 11/1994 | Walker et al. . |
| 5,370,691 | 12/1994 | Samson . |
| 5,383,928 | 1/1995 | Scott et al. . |
| 5,395,349 | 3/1995 | Quiachon et al. . |
| 5,397,345 | 3/1995 | Lazarus . |
| 5,419,324 | 5/1995 | Dillow . |
| 5,464,449 | 11/1995 | Ryan et al. . |
| 5,484,418 | 1/1996 | Quiachon et al. . |
| 5,489,295 | 2/1996 | Piplani et al. . |
| 5,545,208 | 8/1996 | Wolff et al. .................................. 623/1 |
| 5,562,726 | 10/1996 | Chuter . |
| 5,562,728 | 10/1996 | Lazarus et al. . |
| 5,578,075 | 11/1996 | Dayton ........................................ 623/1 |
| 5,632,772 | 5/1997 | Alcime et al. . |

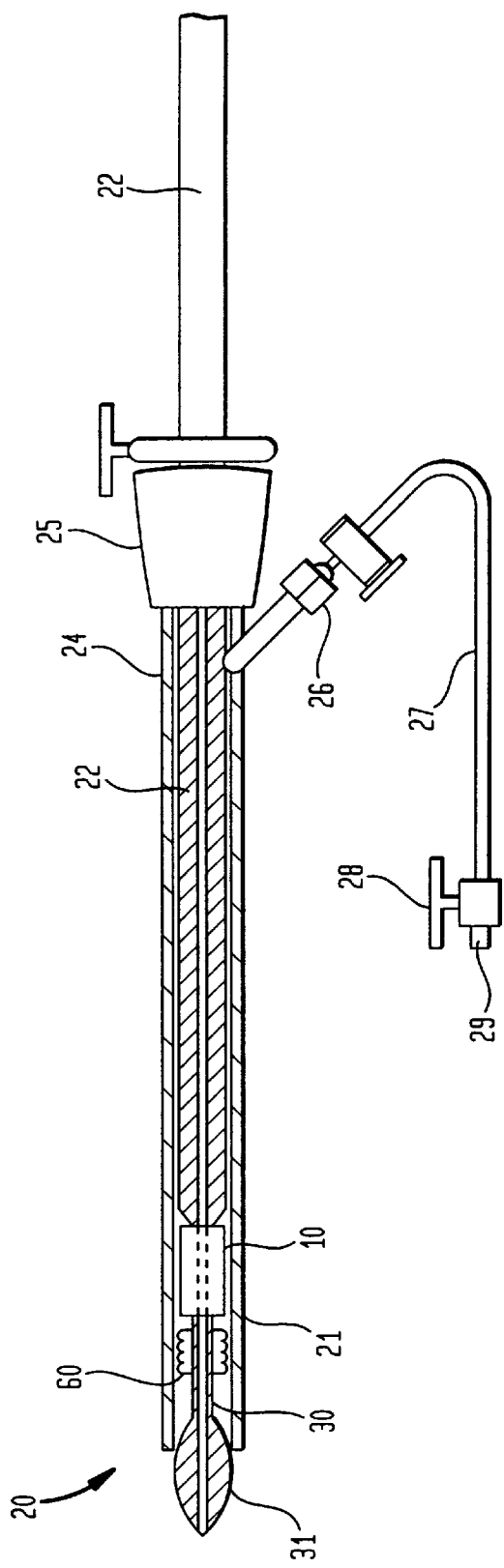
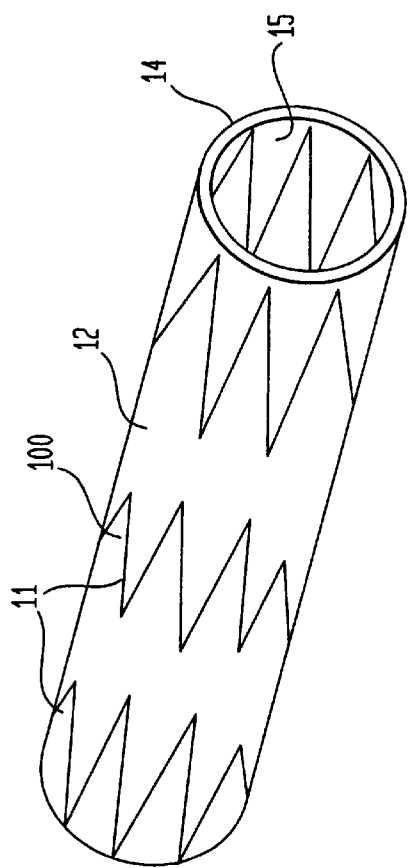

SELF-EXPANDING ENDOLUMINAL PROSTHESIS

This application is a continuation of U.S. patent application Ser. No. 08/485,015 filed Jun. 7, 1995 abandoned.

FIELD OF THE INVENTION

The present invention relates in general to a self-expanding endoluminal prosthesis for use within a body passageway or duct. The invention relates in particular to such a prosthesis that is useful in the treatment of small calibre blood vessels that are aneurysmatic or narrowed or occluded by disease.

BACKGROUND OF THE INVENTION

Endoluminal endovascular grafting has developed as an alternative to conventional vascular surgery. It involves the placement of a prosthesis within a body lumen, such as a blood vessel or other body duct. This obviates the need for surgically incising, removing, replacing, or bypassing a defective vessel.

With endoluminal grafting, the first step is to access the defective vessel either percutaneously or using surgical cut-down techniques. (Percutaneous entry is through the skin, and surgical cut-down entry is directly into an artery itself, which has been surgically exposed.

After accessing the vessel, a tubular prosthesis is delivered, by catheter, to a particular location within the vessel. Typically, a prosthesis is either a stent with a fabric graft covering or a stent alone. The prosthesis is deployed at the desired location where it expands to a predetermined size and presses outwardly against the lumen walls of the vessel.

A particular use of endoluminal endovascular grafting is to hold arteries open after angioplasty or atherectomy. Arteries treated by such procedures are subject to restenosis, dissections, and intimal flap formation, which can impede blood flow. An artery treated by angioplasty or atherectomy may also show elastic recoil and later restenosis. Another use is to create a new wall inside an aneurysmatic artery.

The use of vascular stents alone (without a graft covering) has been shown to control elastic recoil and formation of intimal flaps. Two main types of stents are currently available: a balloon-expandable type, made from a malleable metal, and a self-expanding type made from an elastic metal.

The balloon-expandable types are usually made from malleable stainless steel or tantalum. Such a stent is disclosed in U.S. Pat. No. 5,133,732, issued to Wiktor. The malleability of the metal allows the stent to be compressed around an angioplasty balloon, and expanded at the correct location in the vasculature by inflating the balloon.

The advantage of balloon-expandable stents is the ability to be expanded to an exact size simply by choosing a correct balloon size. Such stents can be tailored to fit the diameter of the lumen of the vessel.

A disadvantage of such stents, however, is that they are non-elastic and non-compliant. If they are crushed or kinked by an external force, they do not recover their shape. If they are physically crushed, they remain crushed. Further angioplasty is required in order to re-establish blood flow.

In addition, if they are overdialated during angioplasty, they remain overdialated. If such stents are covered with fabric grafts of Dacron\ or polytetrafluoroethylene (PTFE), the fabric that is overexpanded remains overexpanded. This creates creases that can push the stent into the lumen or protrude through the stent frame into the lumen.

Furthermore, such stents shorten in length when they are released by as much as 30%. Angioplasty cannot remedy these problems.

Elastic stents made from stainless steel are self-expanding and remain elastic and compliant. For stents made from normal spring metals, however, it is difficult to control the outward force on the vessel wall. According to Hook's law of elasticity, the outward force exerted by elastic stents made of spring metals increases with the amount of stent compression.

To address this problem, it is known to use nitinol as the material from which a stent is made. Nitinol removes the problem of variable outward force because it has the property, at body temperature, of pseudoelasticity, or superelasticity. In the superelastic state, and within certain limits, the outward force exerted by a nitinol stent remains constant, regardless of the strain in the stent.

A disadvantage of stents, however, is that tissue can grow from the lumen walls through the spaces defined by the wire forming the stents. In order to prevent such tissue ingrowth, fabric grafts have been developed to cover a stent. Materials used or advocated for this purpose include: woven or knitted polyester, PTFE, polyurethane, and other elastomeric polymers.

Some fabric covering materials, however, may be thrombogenic and thicker than desired. A thick covering is not suitable for small calibre arteries, such as femeral, renal, popliteal, carotid, and coronary arteries. Such arteries require extremely small diameter prostheses. In addition, small calibre arteries often have geometric configurations making it difficult to suitably open the artery with a prosthesis. For example, the artery may taper, preventing a prosthesis from being inserted.

U.S. Pat. No. 5,123,917, issued to Lee, describes a method of trapping a scaffold member between two separate tubes which are bonded together. This multi-part construction adds thickness to the graft and has the possible disadvantage of breakdown of the bonding adhesive with the resultant separation of the various parts of the structure.

Other patents, such as U.S. Pat. No. 5,282,824, issued to Gianturco, and U.S. Pat. No. 4,739,762, issued to Palmaz, describe stents that are embedded in a sleeve of plastic covering the outer surface of the stent. Such devices have the disadvantage discussed above of exposure of the inner surface of the stent to the blood in the vessel, thus presenting an uneven surface contributing to turbulent flow.

None of the known devices is a satisfactory prosthesis for use in small calibre arteries. A prosthesis that is small enough and flexible enough for use in such arteries is desirable.

SUMMARY OF THE INVENTION

The present invention is an endovascular prosthesis formed of a support member with or without a continuous skin totally encapsulating the support member. The skin can include drugs or other leaching agents, or radiopaque material. A portion of the prosthesis can be tapered to fit within a tapered artery. The prosthesis is particularly adapted for use in small calibre arteries.

BRIEF DESCRIPTION OF THE DRAWINGS

FIG. 5 is a partial cross-sectional view of an exemplary introducer used to insert the prosthesis of the present invention into a body.

FIG. 6 is a perspective view of another alternative embodiment of the present invention.

DETAILED DESCRIPTION OF THE INVENTION

Parent application Ser. No. 08/485,015, filed Jun. 7, 1995 is incorporated by reference herein, in its entirety.

The present invention involves a self-expanding endoluminal prosthesis having an inert, biologically stable skin and an elastic stiffening material, or stent, used as a support member, that is totally encapsulated between the inner and outer walls of the skin. This produces an endoluminal prosthesis in which the stent is totally isolated from the blood vessel wall and the blood stream. Only the inert skin is in contact with the blood. Because the stent is totally encapsulated, the inner surface of the prosthesis is very smooth and creates minimal turbulence in the blood vessel.

The prosthesis of the present invention may also be used without the skin in small calibre arteries or vessels where branch vessels intersect with the arteries in which the stent is deployed at the location of the stent. This allows blood to flow to the branch arteries.

The endoluminal prosthesis of the invention may also be configured to the shape of the blood vessel, or other body lumen, in which it is deployed. For example, where the coronary arteries taper from a diameter of approximately four to six millimeters to approximately three millimeters, known prostheses of uniform diameter do not adequately fit the tapered section. The prosthesis of the present invention may be tapered such that it has a changing diameter that conforms to the shape of the artery. The prosthesis diameter may also expand to fit expanding sections of the arteries. The endoprosthesis of the invention may be over-expanded if necessary when excessive arteriosclerotic build-up is present. This provides the advantage of allowing the prosthesis to overdialate momentarily and then return to its memory shape.

Figure 1:
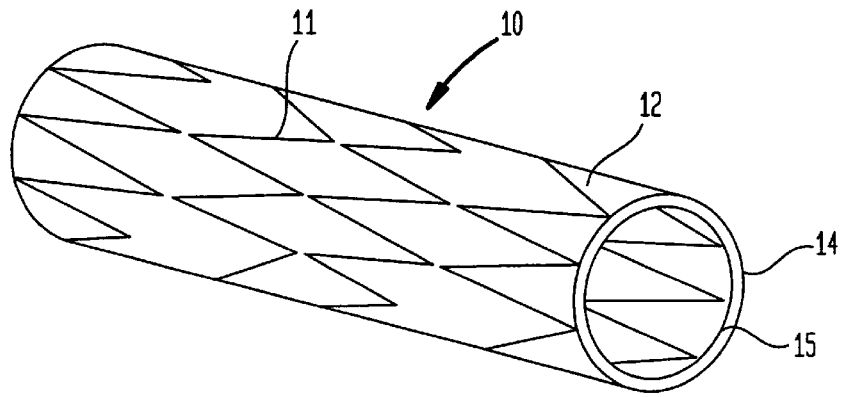
FIG. 1 is a perspective view of an exemplary prosthesis according to the present invention.
Figure 2:
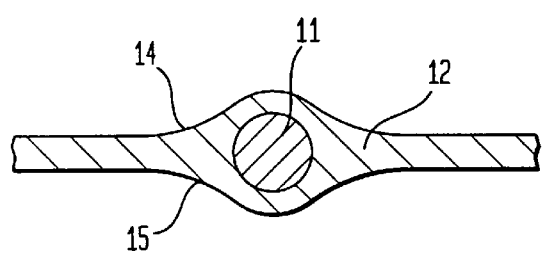
FIG. 2 is a partial, exploded, cross-sectional view of the prosthesis shown in FIG. 1.
Figure 3:
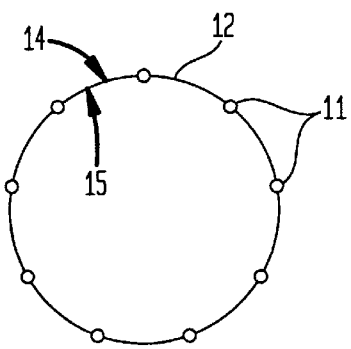
FIG. 3 is a cross-sectional view of the prosthesis shown in FIG. 1.

FIG. 1 shows an exemplary graft according to the present invention. Prosthesis 10 is made of stent 11 which is completely encapsulated between outer wall 14 and inner wall 15 of skin 12. FIG. 2 is an exploded cross-sectional view of a portion of prosthesis 10 showing localized swelling which occurs in skin 12 around stent 11 as both outer wall 14 and inner wall 15 expand to accommodate stent 11. FIG. 3 is a cross-sectional view of prosthesis 10.

Stent 11 is preferably a metallic alloy which has both shape memory and superelastic properties. Such an alloy could be nitinol with an austenitic transformation temperature slightly lower than normal body temperature; for example, about 35° C. Stent 11 may be one of a number of different configurations (in which the wire may have a cross section of any shape). These configurations include, but are not limited to, a spirally wound wire as in a coil spring; a continuous zig-zag wire formed into a spiral; a continuous zig-zag wire formed into a plurality of parallel hoops (as in the embodiment illustrated in FIG. 1); a zig-zag wire, made into a single endless discrete hoop; a plurality of discrete hoops arranged serially and encapsulated in the tube; a mesh or braided structure formed from wire; and a mesh structure formed of expanded sheet material with slits in it. Alternatively, stent 11 may be a plastic which may or may not have shape memory properties.

Skin 12 of endoluminal prosthesis 10 may be made from any one of a number of different materials. Preferably, the material is biologically inert, biologically stable for use as a long term implant, capable of being formed into a tubular shape and totally encapsulating a stent member, elastic to give good compliance to the prosthesis, and of high tensile strength in order to maintain stability when formed into very thin sections. Skin 12 may be made as thin as 0.05 mm and still maintain sufficient strength. This allows prosthesis 10 to be extremely thin and elastic, causing minimal disruption to blood flow within a vessel.

Because stent 11 is totally encapsulated by skin 12, there is no need to use sutures or other such means to connect the apices of stent 11 in a zig-zag wire configuration. Such connecting sutures may be eliminated by encapsulating stent 11 entirely within skin 12. This is true even when using discontinuous, discrete zig-zag hoops 100, as shown in FIG. 6. Skin 12 secures all points of stent 11 relative to one another, but allows contraction and expansion of prosthesis 10.

Typically, skin 12 is made of an elastomeric polymer. A suitable material is Chronoflex\, which is bio-stable polyurethane available from PolyMedica Biomaterials Inc., 2 Constitution Way, Woburn, Mass. Chronoflex is an ether-free medical grade polyurethane which has high stability in long term implants.

In the exemplary embodiment depicted in FIG. 1, stent 11 is made of a continuous zig-zag nitinol wire wound into a plurality of concentric hoops and totally encapsulated between inner and outer walls 15 and 14 of skin 12, which is made from Chronoflex AR bio-stable, ether-free polyurethane.

Prosthesis 10 according to the present invention may be formed by insert molding. Stent 11 is first placed in a mold. An elastomeric polymer is then injected into the mold. The injection may be thermoplastic, where the polymer is melted, or the injection may be of a solution of the polymer dissolved in a solvent where the solvent is evaporated as the mold is heated. In either event, the polymer cures around stent 11 to form skin 12.

Alternatively, prosthesis 10 may be formed on a mandrel. A solution of the elastomeric polymer to be used as skin 12 is first prepared in the desired solution strength. The solution is degassed in a vacuum chamber to remove air bubbles. Stent 11 is placed on a mandrel, which is continuously rotated at a slow speed (approximately 70–100 RPM). A solution of the polymer is applied to the rotating mandrel and left until the solvent evaporates. Hot air may be blown over the mandrel to decrease evaporation time. The rotating mandrel may also be placed inside a heated vacuum chamber to decrease evaporation time.

The strength of the polymer solution used in the methods described above affects the coating thickness. A stiff solution produces a thick coating, and a dilute solution produces a thin coating.

The mandrel used in the method described above is preferably very smooth and may be coated with a release agent, in order to expedite removal of the prosthesis from the mandrel. After removal from the mandrel, the prosthesis may be cured in an oven to make sure all solvent is evaporated and the coating is at full strength.

The coating material used for skin 12 may include a radiopaque material, such as barium sulfate or bismuth bicarbonate. Such material may be added to the coating solution in any desired strength, in order to render prosthesis 10, in its entirety, visible under x-rays.

Drugs such as heparin, low molecular weight heparin, anti-microbial agents, anti-bacterial agents, and anti-inflammatory agents may also be incorporated into the polymer coating of skin 12. These drugs leach out slowly over time to produce a time-controlled leaching. Alternatively, the drugs may be bonded to the surface of the polymer by surfactants such as tridodecylmethylammonium chloride (TDMAC).

In order to enhance the effectiveness of prosthesis 10, skin 12 may be porous. This allows tissue to infiltrate the wall of the prosthesis like a filter, and it allows blood to feed the artery wall so that it continues to receive nutrients. The pores may vary in size between 20 and 40 microns. The pores also act as reservoirs for drugs such as anticoagulants, antiplatelets, or others to assist the initial healing and adaptation of the endoprosthesis to its new environment within the artery.

Porosity can be introduced mechanically by drilling holes in skin 12 mechanically or using lasers, or by indirect methods. One such indirect method is to introduce another substance (such as heparin) into skin 12 which leaches out of skin 12 over time. As the substance leaches out, holes are created in skin 12, rendering it porous.

A particularly advantageous use of the prosthesis of the present invention is in small calibre blood vessels. For example, the coronary, femeral, renal, popliteal, carotid, and saphenous arteries are quite narrow and require a very small diameter prosthesis. The prosthesis of the present invention may be made to such a small diameter with a thin skin member. The small size combined with the reduced turbulence in the blood flow produced by this prosthesis render it ideal for use in such arteries. The prosthesis of the present invention is also useful in neurological applications because it is small and flexible enough to be used in the small blood vessels in the brain.

Skin 12 encapsulating stent 11 is flexible enough, and stretched thinly enough, that it constricts and expands diametrically with stent 11. In addition, prosthesis 10 may be made greater than 25 millimeters (for example 30 millimeters) long because of the flexibility of skin 12. Conventional prostheses are only about 16 millimeters or less in length.

By virtue of its flexibility, it is possible to overdialate prosthesis 10 and still have it resume its original shape. The elastic material used for skin 12 is conducive to such behavior, whereas Dacron\ and PTFE, the conventional graft materials, are not.

An alternative exemplary embodiment of the present invention involves using stent 11 without encapsulating skin 12. This embodiment is useful for preventing elastic recoil of the artery. The diameter of the stent is preferably 10 millimeters or less. The small diameter is designed to allow the stent to be placed within one of the small calibre arteries of the body.

Figure 4A:
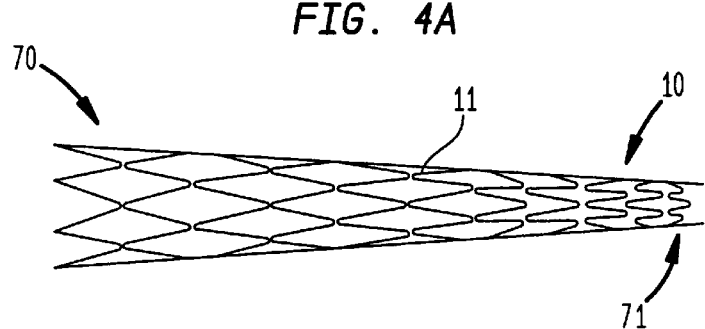
FIGS. 4a and 4b are side views of an alternative embodiment of the present invention.

Another alternative embodiment of the invention involves tapering prosthesis 10, as shown in FIG. 4a. In this embodiment, prosthesis 10 may be formed of stent 11 alone (as in the illustrated embodiment) or of stent 11 encapsulated by a skin (not shown). In either event, prosthesis 10 is designed to fit within a tapered section of an artery. Tapering prosthesis 10 is a significant advancement in the art; conventional stents of uniform diameter cannot be used in geometrically variable arteries. The nonuniform diameter of the prosthesis of the present invention allows the prosthesis to be used in arteries that have a nonuniform diameter.

In the illustrated embodiment, in which the amount of taper is emphasized for illustration, first end 70 of prosthesis 10 may be, for example, four milllimeters in diameter, tapering to second end 71 of, for example 3 millimeters.

A taper may be formed in stent 11 by winding a wire around pins on a tapered mandrel, which is designed to conform to the shape of the artery in which the prosthesis will be used. The shape of the mandrel is imparted to stent 11 by annealing the wire, which is preferably nitinol shape memory alloy, after the wire is wound on the mandrel. The wire is then cooled before removal. When reheated to above its austenitic transition temperature, the wire reforms to the tapered shape imparted to it by the mandrel. A skin may be applied to stent 11 as described above.

Other nonuniform diameter shapes may also be imparted to prosthesis 10. These shapes may include an expanding conical section on one or both ends of the stent, or an expanded diameter section in the center of the stent.

Figure 4B:
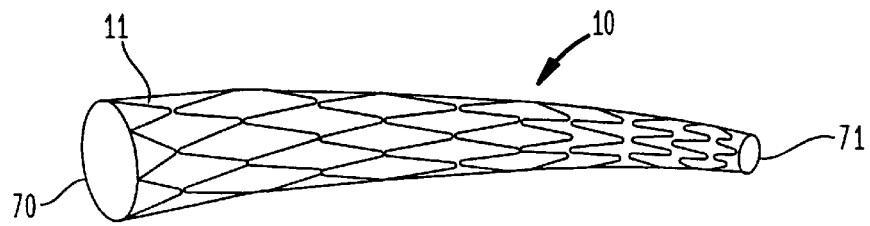

FIG. 4b shows the flexibility of prosthesis 10. This flexibility allows for greater length of the prosthesis because it can conform to curves and other geometric variances in an artery, unlike more rigid known devices.

The prosthesis of the present invention is delivered and deployed to a particular location within the body. An introducer 20, shown in FIG. 5, is used for this purpose. Introducer 20 consists of two concentric tubes. Outer tube 21 is thin-walled and made from a material which is biocompatible and which has a low coefficient of friction. Such a material could be PTFE or polyethylene. Inner tube 22 has a wall thickness such that its outer diameter is slip fit into outer tube 21. The inner diameter of inner tube 22 is just large enough to allow the passage of, for example, a 0.035 inch diameter guide wire (not shown).

Proximal end 24 of outer tube 21 terminates with a sealing device or valve 25 which allows inner tube 22 to slide easily while maintaining a blood tight seal. The seal also allows the clamping of the two tubes together so that no relative movement is possible. A preferred version of such a seal is known as a Touhy-Borst valve. Just distal to valve 25 is a side port 26 and flexible tube 27, terminated in a stop cock 28 and female luer fitting 29. This side port assembly facilitates flushing the system.

The distal end 30 of inner tube 22 has a section of much smaller diameter. Prosthesis 10 and a silicone balloon 60, used for molding prosthesis 10 after insertion, are disposed around this smaller diameter section. The final termination of inner tube 22 is a torpedo-shaped section 31 with a major diameter equal to the diameter of the main section.

In order to insert prosthesis 10 into introducer 20, prosthesis 10 is first cooled in ice water to a temperature below the martensitic transformation temperature of stent 11. When cool, the device is compressed to a reduced diameter around the smaller diameter section of inner tube 22. Skin 12 is thin enough that it contracts with stent 11 as stent 11 is compressed.

Prosthesis 10 on inner tube 22 is then mounted inside outer tube 21. Torpedo-shaped section 31 becomes a "nose cone" which serves to terminate outer tube 21 and provide a smooth transition from a guide wire diameter to the outside diameter of outer tube 21. This smooth transition is required in order to introduce the complete assembly into the body vessel over a guide wire. The rear of the nose cone is tapered to facilitate removal of the inner tube after the device has been expanded.

Introducer 20 is inserted into the vasculature over a guidewire to the desired location. By maintaining inner tube 22 in a fixed position, and withdrawing outer tube 21, prosthesis 10 is discharged from introducer 20 into an artery. Once out of introducer 20, prosthesis 10 is exposed to body temperature, which is above its austenitic temperature. It thus expands to a diameter that allows engagement of the outer wall 14 of graft 12 with the inner walls of the blood vessel.

The blood vessel is held open by prosthesis 10, and blood may flow freely through prosthesis 10 and the artery. Because stent 11 is completely encapsulated between the inner and outer walls 15 and 14 of skin 12 according to one embodiment of the invention, stent 11 is isolated from both the inner walls of the lumen and the blood flowing in the artery.

A particularly useful application of the prosthesis of the present invention is in vessels (such as saphenous veins) that have been transplanted in a patient during, for example, by-pass surgery. In many cases, the implanted vessel occludes or experiences restenosis after implant, requiring anticoagulants or angioplasty. By using the small calibre prostheses of the present invention in the implanted vessel, such procedures may be avoided.

Although this invention has been described with reference to particular embodiments, it is not limited thereto. Rather, it encompasses also such other variants and embodiments as may be devised by those skilled in the art without departing from the spirit and scope thereof. It is intended that the appended claims be construed accordingly.

What is claimed:

1. An endovascular prosthesis comprising a support member defined by a continuous wire bent into a zig-zag configuration and a continuous skin encapsulating said support member to secure all points of the support member relative to one another in the absence of any other securing means while allowing contraction and expansion of the prosthesis.

2. An endovascular prosthesis according to claim 1 wherein said prosthesis is self-expanding.

3. An endovascular prosthesis according to claim 1 wherein said skin is a polymeric material.

4. An endovascular prosthesis according to claim 3 wherein said polymeric material is an elastic, bio-stable polyurethane.

5. An endovascular prosthesis according to claim 1 wherein said support member is nitinol wire.

6. An endovascular prosthesis according to claim 1 wherein said support member is shape memory plastic.

7. An endovascular prosthesis according to claim 1 wherein said skin further includes a radiopaque material.

8. An endovascular prosthesis according to claim 1 wherein said skin further includes a time-controlled leaching substance.

9. An endovascular prosthesis according to claim 8 wherein said substance is selected from the group consisting of heparin, an anti-inflammatory agent, an anti-bacterial agent, and an anti-microbial agent.

10. An endovascular prosthesis according to claim 1 wherein said skin is porous.

11. A method of treating a blood vessel comprising the step of placing within said blood vessel the endovascular prosthesis of claim 1.

12. An endovascular prosthesis as claimed in claim 1 wherein said support member comprises a stent formed from a continuous wire bent into a plurality of concentric hoops, each defined by a zigzag pattern, the resultant configuration having a substantially cylindrical shape, wherein the diameter of said stent is less than 10 millimeters.

13. The endovascular prosthesis according to claim 1 wherein the continuous wire is wound into a plurality of concentric hoops having a circumference substantially perpendicular to an axis of said prosthesis.

14. The endovascular prosthesis according to claim 1 wherein the continuous wire is wound spirally about an axis of said prosthesis.

15. An endovascular prosthesis, as recited in claim 1, wherein said skin includes pores in the range of 20 to 40 microns.

16. The endovascular prosthesis, as recited in claim 15, wherein the pores in said skin form reservoirs for one or more drugs.

17. An endovascular prosthesis as claimed in claim 1 wherein said support member comprises a stent formed from a continuous wire bent into a plurality of concentric hoops, each defined by a zig-zag pattern, the resultant configuration having a substantially cylindrical shape.

18. An endovascular prosthesis comprising a support member defined by a plurality of serially arranged discrete hoops, each hoop comprising a wire bent into a zig-zag configuration, and a continuous skin encapsulating said support member to secure all points of the support member relative to one another in the absence of any other securing means while allowing contraction and expansion of the prosthesis.

* * * * *